United States Patent
Yamamoto et al.

(10) Patent No.: US 8,778,363 B2
(45) Date of Patent: Jul. 15, 2014

(54) OIL-IN-WATER EMULSION SKIN CARE COSMETIC COMPOSITION

(75) Inventors: Rie Yamamoto, Yokohama (JP); Kazuhiko Fujiwara, Yokohama (JP); Ayumi Asai, Yokohama (JP); Tomomi Furukawa, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 73 days.

(21) Appl. No.: 13/322,197

(22) PCT Filed: Dec. 16, 2009

(86) PCT No.: PCT/JP2009/006929
§ 371 (c)(1),
(2), (4) Date: Mar. 20, 2012

(87) PCT Pub. No.: WO2010/137094
PCT Pub. Date: Dec. 2, 2010

(65) Prior Publication Data
US 2012/0172433 A1    Jul. 5, 2012

(30) Foreign Application Priority Data
May 25, 2009    (JP) .................................. 2009-124824

(51) Int. Cl.
*A61K 8/92* (2006.01)
*A61Q 19/00* (2006.01)

(52) U.S. Cl.
USPC .......................................... 424/400; 514/552

(58) Field of Classification Search
CPC ... A94K 2800/592; A94K 8/062; A94K 8/31; A94K 8/8111; A94K 8/922; A61Q 19/08
USPC .......................................... 514/552; 424/400
See application file for complete search history.

(56) References Cited

U.S. PATENT DOCUMENTS

| | | | |
|---|---|---|---|
| 4,226,858 A * | 10/1980 | Pfirrmann et al. | 424/725 |
| 4,820,510 A * | 4/1989 | Arraudeau et al. | 424/63 |
| 4,919,934 A * | 4/1990 | Deckner et al. | 424/401 |
| 6,488,941 B1 | 12/2002 | Burnier et al. | |

FOREIGN PATENT DOCUMENTS

| | | |
|---|---|---|
| EP | 1733711 A1 | 12/2006 |
| JP | 63-096113 | 4/1988 |
| JP | 2004-067622 | 3/2004 |
| JP | 2005-112770 | 4/2005 |
| WO | 00/27346 | 5/2000 |

OTHER PUBLICATIONS

Espacenet bibliographic data for JP 63096113 published Apr. 27, 1988, one page.
Espacenet bibliographic data for JP 2005112770 published Apr. 28, 2005, one page.
Espacenet bibliographic data for JP 2004067622 published Mar. 4, 2004, one page.

* cited by examiner

*Primary Examiner* — Audrea Buckley
(74) *Attorney, Agent, or Firm* — Rankin, Hill & Clark LLP

(57) ABSTRACT

To provide an oil-in-water emulsion skin care cosmetic composition which, without the addition of a pharmaceutical agent and a film-forming agent or the like thereto, effects an excellent elastic or resilient feeling to skin and is excellent in non-stickiness and stability. An oil-in-water emulsion skin care cosmetic composition, comprising (a) a paraffin wax and/or a polyethylene wax, (b) a microcrystalline wax, and (c) an animal/plant-derived wax which contains, as the main ingredient thereof, an ester of a higher fatty acid having from 20 to 32 carbon atoms and an alcohol having from 28 to 34 carbon atoms, and has a melting point of from 75 to 100° C., in which the ratio of component (a) to component (b) is from 70/30 to 95/5 (by mass).

2 Claims, No Drawings

OIL-IN-WATER EMULSION SKIN CARE COSMETIC COMPOSITION

TECHNICAL FIELD

The present invention relates to an oil-in-water (O/W) emulsion skin care cosmetic composition. More precisely, the invention relates to an oil-in-water emulsion skin care cosmetic composition which, without the need for adding a pharmaceutical agent and a film-forming agent or the like thereto, effects an excellent elastic or resilient feeling to skin and is excellent in non-stickiness and stability.

BACKGROUND ART

Heretofore, for delaying or preventing the reduction of skin elasticity or resilience and the appearance of wrinkles due to ageing, etc., and for concealing wrinkles by using a skin care cosmetic composition, there has been known a method of using a pharmaceutical agent of vitamin A or its derivatives or the like (e.g., see Patent References 1 and 2). As an ingredient capable of effecting an elastic or resilient feeling to skin within a short period of time, there has been known a film-forming agent such as polyvinyl alcohol, polyvinyl pyrrolidone, acrylic resin or the like, or a silicone elastomer or the like (e.g., see Patent References 3 to 5).

However, the method of using a pharmaceutical agent requires long-term continuous use of the agent, and according to the method, it is difficult to stably keep the pharmaceutical agent in the base without lowering the efficacy of the pharmaceutical agent. On the other hand, the method of using a film-forming agent or the like has some problems in that, when the agent is added in an amount enough to satisfy the feeling of skin resilience or elasticity, then it may occur the scum or settling come from the applied cosmetic composition and the stickiness in its application onto the skin, that the stability of the agent is poor in long-term storage thereof, and that the agent adversely affects the stability of the other additive ingredients, etc.

PRIOR ART REFERENCES

Patent References

Patent Reference 1: JP 8-245366A
Patent Reference 2: JP 3634139B
Patent Reference 3: JP 2007-269723A
Patent Reference 4: JP 5-933A
Patent Reference 5: JP 9-315936A

SUMMARY OF INVENTION

Problems that Invention is to Solve

The present invention has been made in consideration of the above-mentioned situation, and its object is to provide an oil-in-water emulsion skin care cosmetic composition which, without the need for adding a pharmaceutical agent and a film-forming agent or the like thereto, effects an excellent elastic or resilient feeling to skin and is excellent in non-stickiness and stability.

Means for Solving the Problems

In order to solve the above-mentioned problems, the invention provides an oil-in-water emulsion skin care cosmetic composition which comprises (a) a paraffin wax and/or a polyethylene wax, (b) a microcrystalline wax, and (c) an animal/plant-derived wax which contains as the main ingredient thereof, an ester of a higher fatty acid having from 20 to 32 carbon atoms and an alcohol having from 28 to 34 carbon atoms, and that has a melting point of from 75 to 100° C., wherein the ratio of component (a) to component (b) is from 70/30 to 95/5 (by mass).

The invention also provides the oil-in-water emulsion skin care cosmetic composition, wherein component (c) is carnauba wax.

The invention also provides the oil-in-water emulsion skin care cosmetic composition, wherein the total amount of component (a) and component (b) is from 0.01 to 2% by mass, and the amount of component (c) is from 0.005 to 2% by mass.

Advantageous Effects of Invention

According to the invention, there is provided an oil-in-water emulsion skin care cosmetic composition which, without the addition of a pharmaceutical agent and a film-forming agent or the like thereto, effects an excellent elastic or resilient feeling to skin and is excellent in non-stickiness and stability.

MODE FOR CARRYING OUT INVENTION

The invention is described in detail hereinunder. In the following, "POE" means "polyoxyethylene", and "POP" means "polyoxypropylene".

In the invention, a paraffin wax and/or a polyethylene wax is used as component (a).

The paraffin wax is generally obtained through separation and extraction of a hydrocarbon of good crystallizability from the oily distillate moiety in reduced-pressure distillation of crude oil. It is a colorless or white transparent solid wax containing a linear hydrocarbon as the main ingredient thereof, and that has a mass-average molecular weight (Mw; hereinafter simply referred to as "molecular weight") of from 200 to 700 or so.

The polyethylene wax is a synthetic wax and is a low-molecular-weight ethylene polymer that exhibits a white waxy solid state. In the invention, preferred is use of those having a molecular weight (Mw) of from 300 to 700, especially from 400 to 600 or so. Component (a) may be used either alone or in combination.

The microcrystalline wax as component (b) is mainly a hydrocarbon wax to be taken out from the residual oily moiety in reduced-pressure distillation of crude oil, in which many of the constitutive hydrocarbons are branched hydrocarbons (isoparaffin) and saturated cyclic hydrocarbons (cycloparaffin). Accordingly, as compared with that of the paraffin wax of component (a), the crystal size of the ingredient is small, and the molecular weight thereof is generally from 500 to 800 or so. The melting point of component (b) is from 60 to 90° C. or so. Component (b) is commercially available as "Microcrystalline Wax P" (by Nikko Rica Corp.), etc. Component (b) may be used either alone or in combination.

In the invention, component (a) and component (b) are incorporated in such a blend ratio that (a)/(b) is from 70/30 to 95/5 (by mass). When the ratio of component (a) to component (b) is larger than the above range, then component (a) may readily crystallized because of its high crystallizability, and therefore the stability of the composition becomes poor; but on the other hand, when the ratio is smaller than the range, it tends to occur stickiness.

In the invention, the total amount of component (a) and component (b) is preferably from 0.01 to 2% by mass, more preferably from 0.05 to 1% by mass, most preferably from 0.2 to 0.5% by mass. When the amount is less than 0.01% by mass, then it tends to lose the resilient feeling; but on the other hand, when the amount is more than 2% by mass, then the crystallizability becomes high and the ingredients may readily crystallized, and therefore the stability of the composition becomes poor.

Component (c) is an animal/plant-derived wax comprising, as the main ingredient thereof, an ester of a higher fatty acid having from 20 to 32 carbon atoms and an alcohol having from 28 to 34 carbon atoms (the ester accounts for from about 80 to 85% by mass of component (c)), and having a melting point of from 75 to 100° C. The melting point is preferably from 80 to 90° C. Preferred is a plant-derived wax. In concrete terms, preferred examples include carnauba wax, and rice wax (rice bran wax). Above all, most preferred is carnauba wax.

Candelilla wax is not within the scope of component (c) in the invention, although it is, like carnauba wax, a type of plant-derived wax and is popularly used in cosmetic compositions, as it contains a fatty acid ester having from 16 to 34 carbon atoms in an amount of about 30% by mass, a hydrocarbon such as hentriacontane ($C_{31}H_{64}$) or the like in an amount of about 45% by mass, and a free alcohol, a resin or the like in an amount of about 25% by mass, and has a melting point of from 66 to 71° C.

The amount of component (c) to be incorporated is preferably from 0.005 to 2% by mass in the entire amount of the cosmetic composition of the invention, more preferably from 0.01 to 1% by mass, most preferably from 0.01 to 0.5% by mass. When the amount is less than 0.005% by mass, then it could not prevent the crystallization of component (a) and therefore, the stability of the composition may be poor; but on the other hand, when the amount is more than 2% by mass, the stickiness tends to increase.

The ratio of component (c) to the total amount of component (a) and component (b) (by mass), i.e., (c)/[(a)+(b)] (by mass), is preferably at least 0.02 from the viewpoint of the stability of the composition. The uppermost limit is not specifically defined, but is preferably at most 1 (by mass).

In the cosmetic composition of the invention, the combination of components (a) to (c) allowed the enhancement of the penetration of the composition into skin and of the resilient feeling of skin, and the attainment of the sufficient stability of the composition. Since component (a) exhibits high crystallizability, the combination of component (a) and component (b) only could hardly attain sufficient stability of the composition; however, the incorporation of component (c) thereinto permitted the enhancement of the stability of the composition. Furthermore, not acted upon by a pharmaceutical ingredient such as vitamin A, a film-forming agent, a silicone resin or the like as previously, the composition of the invention could secure an excellent resilient feeling of skin, and could secure good feeling in use (with no stickiness or tackiness) and good stability.

An emulsifying agent is further incorporated in the oil-in-water emulsion skin care cosmetic composition of the invention, in which, however, the emulsifying agent is not specifically defined but may be any one that may be generally incorporated in emulsion cosmetic compositions, such as nonionic surfactants (oleophilic, hydrophilic), anionic surfactants, cationic surfactants, and ampholytic surfactants, etc.

Exemplary oleophilic nonionic surfactants include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerolsorbitan penta-2-ethylhexylate, and diglycerolsorbitan tetra-2-ethylhexylate; (poly)glycerin fatty acid esters, such as glycerin monostearate, and diglycerin monostearate; propyleneglycol fatty acid esters such as propylene glycol monostearate; hydrogenated castor oil derivatives, and glycerin alkyl ethers.

Exemplary hydrophilic nonionic surfactants include POE sorbitan fatty acid esters, such as POE sorbitan monooleate, POE sorbitan monostearate, POE sorbitan monolaurate, and POE sorbitan tetraoleate; POE sorbitol fatty acid esters, such as POE sorbitol monolaurate, POE sorbitol monooleate, POE sorbitol pentaoleate, and POE sorbitol monostearate; POE glycerin fatty acid esters, such as POE glycerin monostearate, and POE glycerin triisostearate; POE fatty acid esters such as POE monooleate; POE alkyl ethers such as POE lauryl ether; POE alkylphenyl ethers such as POE octylphenyl ether; POE/POP alkyl ethers such as POE/POP cetyl ether; tetra-POE/tetra-POP ethylenediamine condensates, POE castor oil or hardened castor oil derivatives, POE bees wax/lanolin derivatives, alkanolamides such as lauric acid monoethanolamide, POE propylene glycol fatty acid esters, POE alkylamines, POE fatty acid amides, sucrose fatty acid esters, POE nonylphenyl-formaldehyde condensates, alkylethoxydimethylamine oxides, and trioleylphosphoric acid.

Exemplary anionic surfactants include fatty acid soaps, such as soap base, lauric acid salts (salts with sodium, potassium, magnesium, ammonium, monoethanolamine, triethanolamine or the like—the same shall apply hereinunder), and palmitic acid salts; higher alkylsulfate salts such as lauryl sulfate salts; alkyl ether sulfate salts such as POE lauryl sulfate salts; N-acyl sarcosine acid salts such as lauroylsarcosine salts; phosphate salts, such as POE oleyl ether phosphate salts, and POE stearyl ether phosphate salts; sulfosuccinic acid salts, such as di-2-ethylhexyl-sulfosuccinic acid salts, monolauroyl-monoethanolamide-polyoxyethylene-sulfosuccinic acid salts, and laurylpolypropylene glycol sulfosuccinic acid salts; alkylbenzenesulfonic acid salts such as linear dodecylbenzenesulfonic acid salts; N-acylglutamic acid salts, such as N-lauroylglutamic acid salts, and N-myristoyl-L-glutamic acid salts; N-acylglutamic acid salts, such as N-lauroylglutamic acid salts, N-myristoylglutamic acid salts, and N-stearoylglutamic acid salts; N-acylglycine salts, such as N-lauroylglycine salts, N-myristoylglycine salts, and N-stearoylglycine salts; N-acylalanine salts, such as N-lauroylalanine salts, N-myristoylalanine salts, and N-stearoylalanine salts; N-acylaspartic acid salts, such as N-lauroylaspartic acid salts, N-myristoylaspartic acid salts, and N-stearoylaspartic acid salts; long-chain acyl-lower alkyl-type taurine salts, such as N-cocoyl-N-methyltaurine salts, N-lauroyl-N-methyltaurine salts, N-myristoyl-N-methyltaurine salts, N-stearoyl-N-methyltaurine salts, and N-cocoyl-taurine salts; hydroxyether-carboxylic acid salts such as dodecane-1,2-diol acetate ether salts; higher fatty acid ester sulfate salts such as hydrogenated coconut oil fatty acid glycerin sulfate salts; sulfated oils such as Turkey red oil; POE alkyl ether-carboxylic acid salts, POE alkylallyl ether-carboxylic acid salts, α-olefinsulfonic acid salts, higher fatty acid ester sulfonic acid salts, dialcohol sulfate salts, higher fatty acid alkylolamide sulfate salts, lauroylmonoethanolamide succinic acid salts, and N-palmitoylaspartic acid disalts.

Exemplary cationic surfactants include alkyltrimethylammonium salts, such as stearyltrimethylammonium chloride, and lauryltrimethylammonium chloride; dialkyldimethylammonium salts such as distearyldimethylammonium chloride; alkylpyridinium salts, such as poly(N,N'-dimethyl-3,5-methylenepiperidinium) chloride, and cetylpyridinium chloride; alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, benzalkonium chloride, and benzetonium chloride.

Exemplary ampholytic surfactants include imidazoline-type ampholytic surfactants, such as 2-undecyl-N,N,N-(hydroxyethylcarboxymethyl)-2-imidazoline sodium, and 2-cocoyl-2-imidazoliniumhydroxide-1-carboxyethyloxy 2-sodium salt; betaine-type surfactants, such as 2-heptadecyl-N-carboxymethyl-N-hydroxyethylimidazolinium betaine, betaine lauryldimethylaminoacetate, alkylbetaine, amidebetaines, and sulfobetaine.

As the emulsifying agent in the invention, preferred is a nonionic surfactant alone, or a combination of a nonionic surfactant and an anionic surfactant, especially a long-chain acyl-lower alkyl-type taurine-type anionic surfactant (for example, stearoylmethyltaurine salt, etc.), from the viewpoint of the stability or the like of the composition.

The oil-in-water emulsion skin care cosmetic composition of the invention may suitably contain, if desired in addition to the above-mentioned ingredients, any other optional additive ingredient generally used in external applications for skin care such as ordinary cosmetic products or medicinal products, etc., within a range not detracting from the object and the advantages of the invention. For example, the optional ingredient includes, but not limited thereto, oils and fats, waxes, hydrocarbon oils, higher fatty acids, higher alcohols, synthetic ester oils, silicone oils, water-soluble polymers, chelating agents, lower alcohols, polyalcohols, pH-regulating agents, antioxidants, powdery ingredients, fragrance, and water.

Exemplary oils and fats include liquid oils and fats, such as corn oil, olive oil, rapeseed oil, castor oil, soybean oil, peanut oil, and glycerin triisooctanoate; solid oils and fats, such as cacao butter, and hydrogenated oil.

Exemplary waxes include bees wax and lanolin.

Exemplary hydrocarbon oils include liquid paraffin, squalane, ceresine, vaseline, and paraffin.

Exemplary higher fatty acids include lauric acid, myristic acid, palmitic acid, stearic acid, behenic acid, oleic acid, undecylenic acid, tolic acid, isostearic acid, linolic acid, linolenic acid, eicosapentaenoic acid (EPA), and docosahexaenoic acid (DHA).

Exemplary higher alcohols include linear alcohols, such as lauryl alcohol, cetyl alcohol, stearyl alcohol, behenyl alcohol, myristyl alcohol, oleyl alcohol, and cetostearyl alcohol; branched alcohols, such as monostearylglycerin ether (batyl alcohol), 2-decyltetradecinol, lanolin alcohol, cholesterol, phytosterol, hexyldodecanol, isostearyl alcohol, and octyldodecanol.

Exemplary synthetic ester oils include isopropyl myristate, octyldodecyl myristate, myristyl myristate, isopropyl palmitate, hexyl laurate, decyl oleate, oleyl oleate, cetyl lactate, isocetyl isostearate, diisopropyl adipate, diethyl sebacate, diisopropyl sebacate, and crotamiton ($C_{13}H_{17}NO$).

Exemplary silicone oils include linear polysiloxanes, such as dimethylpolysiloxane and methylphenylpolysiloxane.

Exemplary water-soluble polymers include plant polymers, such as carrageenan, pectin, and corn starch; microorganismic polymers, such as xanthane gum, pullulane, and sodium hyaluronate; cellulosic polymers, such as methyl cellulose, ethyl cellulose, hydroxyethyl cellulose, hydroxypropyl cellulose, carboxymethyl cellulose, and sodium carboxymethyl cellulose; alginic acid polymers such as sodium alginate; vinylic polymers, such as polyvinyl alcohol, polyvinyl pyrrolidone, and carboxyvinyl polymer; and acrylic acid polymers, such as sodium polyacrylate, polyethyl acrylate, and polyacrylamide.

Exemplary chelating agents include sodium edetate and sodium metaphosphate.

Exemplary lower alcohols include ethanol and isopropanol.

Exemplary polyalcohols include dialcohols, such as propylene glycol and 1,3-butylene glycol; trialcohols, such as glycerin and 1,2,6-hexanetriol; tetralcohols such as pentaerythritol; pentalcohols such as xylitol; hexylcohols, such as sorbitol and mannitol; polyalcohol polymers, such as dipropylene glycol, triethylene glycol, and polyethylene glycol; and sugar alcohols, such as sorbitol and mannitol.

Exemplary pH regulating agents include buffers, such as lactic acid-sodium lactate and citric acid-sodium citrate; amino acids such as glycine.

Exemplary antioxidants include dibutylhydroxytoluene (BHT) and butylhydroxyanisole (BHA).

Exemplary powder ingredients include inorganic powders, such as talc, kaolin, bentonite, magnesium aluminate silicate, silicic anhydride, titanium oxide, and zinc oxide; organic powders such as cellulose powder; inorganic pigments, such as iron sesquioxide, yellow iron sesquioxide, and black iron oxide; and organic pigments such as aluminium lake.

Other incorporable ingredients include preservatives, such as ethylparaben and butylparaben; antiinflammatory agents, such as glycyrrhizinate derivatives, glycyrrhetinate derivatives, salicylic acid derivatives, and allantoin; vitamins, such as vitamin B6, vitamin C, vitamin E and their derivatives, and panthenol; various extracts, such as *Rosa roxburghii, Achillea millefolium*, melilot, *Phellodendoron amurense* Ruprecht, *Cpotis japonica, Lithospermum erythrorhizon*, Chinese peony, *Swertia japonica*, birch, sage, loquat, ginseng, aloe, *Malva sylvestris*, iris, grape, *coix* seed, sponge cucumber, lily, saffron, *Cnidium rhizome*, ginger, *Hypericum erectum, Ononis spinosa*, garlic, capsicum, Chenpi, *Angelica acutiloba*, and algae; blood circulation promoters, such as vanillylamide nonylate and benzyl nicotinate; fresheners, such as l-menthol and eucalyptus oil; skin-whitening agents (e.g., hydroquinone derivatives such as arbutin; kojic acid, tranexamic acid and their derivatives, etc.); antioxidants, such as thiotaurine, glutathione, catechin, albumin, ferritin, and metallothionein; and UV absorbents, such as benzoic acid-type UV absorbents, salicylic acid-type UV absorbents, cinnamic acid-type UV absorbents, and benzophenone-type UV absorbents.

The oil-in-water emulsion skin care cosmetic composition of the invention can be obtained according to an ordinary method of, for example, by previously preparing an oily phase and an aqueous phase, and thereafter gradually adding the oily phase to the aqueous phase, followed by emulsifying them by mixing, stirring or the like, but not limited thereto. In the cosmetic composition of the invention, preferably, the aqueous phase accounts for from 60 to 97% by mass and the oily phase accounts for from 3 to 40% by mass.

In the invention, the cosmetic composition effects an excellent resilient feeling to skin, without the need for incorporating thereinto any ordinary film-forming agent (e.g., polyvinyl alcohol, polyvinyl pyrrolidone, and acrylic resin), vitamin A or its derivative, and a silicone elastomer or the like, in an amount necessary for making a good recovery of resilient feeling or for enhancing the resilient feeling. However, the invention does not exclude the addition of a small amount of such an ordinary resilient feeling-recovering ingredient as an optional additive ingredient to the cosmetic composition of the invention.

The oil-in-water emulsion skin care cosmetic composition of the invention is widely applicable to cosmetic products, medicinal products and quasi drugs to be applied to the skin.

The composition may have any desired form of products, including emulsion products such as emulsion foundations, and sunscreen emulsions; creamy products such as skin creams, etc.

EXAMPLES

The invention is described more concretely with reference to the following Examples, by which, however, the invention is not limited at all. Unless otherwise specifically indicated, the amount is described in terms of % by mass.

[State Stability]

After samples were prepared, each sample was tested for the presence or absence of its abnormality such as aggregation or coalescence of emulsified particles, crystal deposition, etc., by microscopic observation, and evaluated it according to the following evaluation criteria.

(Evaluation Criteria)
○ (good): No abnormality was observed.
Δ (somewhat bad): Slight abnormality was observed.
x (bad): Apparent abnormality was observed.

[Resilient Feeling]

Ten women expert panelists applied each sample onto their skin and evaluated the resilient feeling of the skin after application according to the following evaluation criteria.

(Evaluation Criteria)
○ (good): Seven or more panelists admitted the resilient feeling.
Δ (somewhat bad): From 3 to 6 panelists admitted the resilient feeling.
x (bad): Two or less panelists admitted the resilient feeling.

[Non-Stickiness]

Ten women expert panelists applied each sample onto their skin and evaluated the non-stickiness of the skin after application according to the following evaluation criteria.

(Evaluation Criteria)
○ (good): Seven or more panelists admitted the non-stickiness.
Δ (somewhat bad): From 3 to 6 panelists admitted the non-stickiness.
x (bad): Two or less panelists admitted the non-stickiness.

Examples 1 to 6, Comparative Examples 1 to 5

Samples each containing the ingredients shown in the following Tables 1 and 2 in the blend ratio also shown therein were prepared according to an ordinary method. The prepared samples were evaluated according to the above-mentioned evaluation methods for the stability (state stability), the resilient feeling and the non-stickiness. The results are shown in Tables 1 and 2.

TABLE 1

| | Example | | | | | |
|---|---|---|---|---|---|---|
| | 1 | 2 | 3 | 4 | 5 | 6 |
| Polyethylene Wax | 0.32 | 0.4 | — | 0.45 | 0.4 | 0.64 |
| Paraffin Wax | — | — | 0.5 | — | — | — |
| Microcrystalline Wax | 0.08 | 0.1 | 0.03 | 0.05 | 0.1 | 0.16 |
| Carnauba Wax | 0.2 | 0.02 | 0.02 | 0.5 | 0.1 | 0.1 |
| Behenyl Alcohol | 0.8 | 0.6 | 0.5 | 0.4 | 2 | 0.6 |
| Stearyl Alcohol | — | — | 0.15 | 0.3 | — | 0.2 |
| Batyl Alcohol | — | — | — | — | 1 | — |
| Palm Oil | 0.5 | 0.5 | 0.8 | 0.5 | 0.5 | — |
| Mineral Oil | 4.5 | 3 | 2.5 | 3 | — | 3.5 |
| Pentaerythrityl Tetraethylhexanoate | 2 | 2.5 | 3 | 3 | 6 | 3 |

TABLE 1-continued

| | Example | | | | | |
|---|---|---|---|---|---|---|
| | 1 | 2 | 3 | 4 | 5 | 6 |
| Dimethicone | 1 | 1 | 0.1 | 1.5 | 2.5 | 1 |
| PEG-60 Glyceryl Isostearate | — | — | — | — | 1.5 | — |
| Sodium Stearoyl-methyltaurine | 0.2 | 0.15 | 0.15 | 0.2 | — | 0.15 |
| Glyceryl Stearate | 0.3 | 0.3 | 0.2 | 0.2 | 1.5 | 0.2 |
| Ethanol | — | — | — | — | 5 | — |
| Carboxyvinyl Polymer | 0.1 | 0.1 | 0.1 | 0.15 | — | 0.12 |
| Potassium Hydroxide | — | — | — | — | 0.03 | 0.03 |
| Xanthan Gum | 0.05 | 0.1 | 0.02 | — | 0.1 | 0.05 |
| Polyvinyl Alcohol | 0.2 | — | 0.2 | — | — | — |
| Glycerin | 3 | 5 | 10 | 15 | 2 | 3 |
| Butylene Glycol | 8 | 5 | 15 | 10 | 6 | 5 |
| Tranexamic Acid | 2 | 2 | 2 | 2 | — | — |
| Potassium 4-Methoxysalicylate | — | — | — | — | 1 | — |
| Citric Acid | 0.05 | 0.05 | 0.05 | 0.05 | 0.01 | 0.01 |
| Sodium Citrate | 0.05 | 0.05 | 0.05 | 0.05 | 0.09 | 0.09 |
| Phenoxyethanol | 0.5 | 0.5 | 0.5 | 0.5 | 0.4 | 0.5 |
| Trisodium Edetate | 0.1 | 0.01 | 0.03 | 0.03 | 0.1 | 0.01 |
| Pure Water | bal. | bal. | bal. | bal. | bal. | bal. |
| State Stability | ○ | ○ | ○ | ○ | ○ | ○ |
| Resilient Feeling | ○ | ○ | ○ | ○ | ○ | ○ |
| Non-stickiness | ○ | ○ | ○ | ○ | ○ | ○ |

TABLE 2

| | Comparative Example | | | | |
|---|---|---|---|---|---|
| | 1 | 2 | 3 | 4 | 5 |
| Polyethylene Wax | 0.32 | — | — | 0.32 | — |
| Paraffin Wax | — | — | — | — | 0.48 |
| Microcrystalline Wax | 0.08 | 0.5 | — | 0.08 | 0.22 |
| Carnauba Wax | — | — | — | — | 0.1 |
| Candelilla Wax | — | — | — | 0.2 | — |
| Behenyl Alcohol | 0.8 | 0.8 | 0.8 | 0.8 | 0.8 |
| Palm Oil | 0.5 | 0.5 | 0.5 | 0.5 | 0.5 |
| Mineral Oil | 4.5 | 4.5 | 4.5 | 4.5 | 4.5 |
| Pentaerythrityl Tetraethylhexanoate | 2 | 2 | 2 | 2 | 2 |
| Dimethicone | 1 | 1 | 1 | 1 | 1 |
| Sodium Stearoylmethyltaurine | 0.2 | 0.2 | 0.2 | 0.2 | 0.2 |
| Glyceryl Stearate | 0.3 | 0.3 | 0.3 | 0.3 | 0.3 |
| Carboxyvinyl Polymer | 0.1 | 0.1 | 0.1 | 0.1 | 0.1 |
| Xanthan Gum | 0.05 | 0.05 | 0.05 | 0.05 | 0.05 |
| Polyvinyl Alcohol | 0.2 | 0.2 | 0.5 | 0.2 | 0.2 |
| Glycerin | 3 | 3 | 3 | 3 | 3 |
| Butylene Glycol | 8 | 8 | 8 | 8 | 8 |
| Citric Acid | 0.01 | 0.01 | 0.01 | 0.01 | 0.01 |
| Sodium Citrate | 0.09 | 0.09 | 0.09 | 0.09 | 0.09 |
| Phenoxyethanol | 0.5 | 0.5 | 0.5 | 0.5 | 0.5 |
| Trisodium Edetate | 0.01 | 0.01 | 0.01 | 0.01 | 0.01 |
| Pure Water | bal. | bal. | bal. | bal. | bal. |
| State Stability | Δ | ○ | Δ | Δ | ○ |
| Resilient Feeling | ○ | Δ | ○ | ○ | ○ |
| Non-stickiness | ○ | x | x | ○ | x |

As obvious from the results in Tables 1 and 2, Examples 1 to 6 satisfying the constituent requirements of the invention achieved excellent advantageous effects in point of all the stability, the resilient feeling and the non-stickiness. On the other hand, Comparative Examples 1 to 5 lacking any of the constituent requirements of the invention could not achieve the advantageous effects of the invention. For example, Comparative Example 3, which did not contain any one of components (a) to (c) and contained an ordinary film-forming agent for the intension of attaining a resilient feeling of skin, could not achieve the non-stickiness and could not satisfy stability. In Comparative Example 4, in which candelilla wax was incorporated in place of component (c), the stability of the sample was poor. Comparative Example 1, which did not contain component (c), was poor in its stability. Comparative Example 2, which contained component (b) but did not contain component (a) and component (c), could not achieve the non-stickiness and was poor in the resilient feeling of the skin. Comparative Example 5, which contained components (a) to (c), however, the blend ratio of component (a) to component (b) was smaller than the range of the invention, could not obtain non-stickiness.

Formulation Examples of the oil-in-water emulsion skin care cosmetic composition of the invention are shown below.

Example 7

O/W Milky Emulsion

| (Ingredients) | (mas %) |
| --- | --- |
| (1) Behenyl Alcohol | 0.8 |
| (2) Batyl Alcohol | 0.1 |
| (3) Polyethylene Wax | 0.4 |
| (4) Microcrystalline Wax | 0.1 |
| (5) Carnauba Wax | 0.1 |
| (6) Glyceryl Stearate | 0.2 |
| (7) Pentaerythritol tetra-2-ethylhexanoate | 3 |
| (8) Dimethicone | 0.5 |
| (9) Squalane | 3 |
| (10) Sodium Stearoylmethyltaurine | 0.2 |
| (11) Glycerin | 5 |
| (12) 1,3-Butylene Glycol | 7 |
| (13) Tranexamic Acid | 2 |
| (14) Sodium Carboxyvinyl Polymer | 0.1 |
| (15) Sodium Metaphosphate | 0.01 |
| (16) Phenoxyethanol | 0.5 |
| (17) Pure Water | bal. |

(Production Method)
The aqueous phase and the oily phase are heated at 70° C., thereafter emulsified with a homomixer and then cooled.

Example 8

O/W Cream

| (Ingredients) | (mas %) |
| --- | --- |
| (1) Polyethylene Wax | 0.4 |
| (2) Microcrystalline Wax | 0.1 |
| (3) Carnauba Wax | 0.02 |
| (4) Sorbitan POE(20) Isostearate | 2.5 |
| (5) PEG-100 Stearate | 0.5 |
| (6) Glyceryl Stearate | 1.2 |
| (7) Behenyl Alcohol | 1.5 |
| (8) Stearyl Alcohol | 0.5 |
| (9) Mineral Oil | 4 |
| (10) Cetyl Ethylhexanoate | 4 |
| (11) Pentaerythrityl Tetraoctanoate | 4 |
| (12) Dimethicone | 3 |
| (13) Bentonite | 0.3 |
| (14) Glycerin | 15 |
| (15) Dipropylene Glycol | 8 |
| (16) Dipotassium Glycyrrhizinate | 0.1 |
| (17) Sodium Metaphosphate | 0.1 |
| (18) Phenoxyethanol | 0.5 |
| (19) Citric Acid | 0.01 |
| (20) Sodium Citrate | 0.09 |
| (21) Pure Water | bal. |

(Production Method)
The aqueous phase and the oily phase are heated at 70° C., thereafter emulsified with a homomixer and then cooled.

INDUSTRIAL APPLICABILITY

According to the invention, there is provided an oil-in-water emulsion skin care cosmetic composition which, without the addition of a pharmaceutical agent and a film-forming agent or the like thereto, effects an excellent elastic or resilient feeling to skin and is excellent in non-stickiness and stability.

The invention claimed is:

1. An oil-in-water emulsion skin care cosmetic composition, comprising:
   (a) a paraffin wax and/or a polyethylene wax,
   (b) a microcrystalline wax, and
   (c) an animal/plant-derived wax which contains an ester of a fatty acid having from 20 to 32 carbon atoms and an alcohol having from 28 to 34 carbon atoms, and has a melting point of from 75 to 100° C., wherein the ratio of the component (a) to the component (b) is from 70/30 to 95/5 by mass and wherein the total amount of the component (a) and the component (b) is from 0.01 to 2% by mass, and the amount of the component (c) is from 0.005 to 2% by mass of the emulsion.

2. The oil-in-water emulsion skin care cosmetic composition as claimed in claim 1, wherein the component (c) is carnauba wax.

* * * * *